United States Patent
Nur

(10) Patent No.: US 8,399,030 B1
(45) Date of Patent: Mar. 19, 2013

(54) SKIN TREATMENT COMPOSITIONS AND METHODS OF USE

(76) Inventor: Waeil Ali Nur, Callaway, VA (US)

( * ) Notice: Subject to any disclaimer, the term of this patent is extended or adjusted under 35 U.S.C. 154(b) by 0 days.

(21) Appl. No.: 13/429,306

(22) Filed: Mar. 23, 2012

(51) Int. Cl.
*A01N 65/00* (2009.01)

(52) U.S. Cl. ........................................ 424/725

(58) Field of Classification Search ................ None
See application file for complete search history.

(56) References Cited

U.S. PATENT DOCUMENTS

| | | | |
|---|---|---|---|
| 2,034,405 A | 3/1936 | MacLaren | |
| 2,334,239 A | 11/1942 | Barnett | |
| 4,271,182 A | 6/1981 | Sullivan | |
| 6,911,196 B2 | 6/2005 | Hamtini | |
| 2004/0053860 A1 | 3/2004 | Buchholz | |
| 2006/0286054 A1 | 12/2006 | Gomez | |

*Primary Examiner* — Michael Meller
(74) *Attorney, Agent, or Firm* — The Gray Law Group, Ltd.; Steven L. Fisher-Stawinski

(57) ABSTRACT

A new use of castor oil in treating atopic eczema and cradle cap is disclosed. Compositions of greater than 50% castor oil and less than 50% mineral oil are preferable for skin application. Compositions of approximately 80% castor oil and 20% mineral oil are optimal for skin application. The compositions are best applied using a small pump-spray bottle (optimally about 2 oz.) having a relatively small output aperture (optimally about 3 mm). The spray application and composition reduced the messiness of the application process.

The composition is applied differently to different conditions; specifically the composition is applied to atopic eczema and dry or non-oily cradle cap and left in place to be absorbed into the patient's skin; to oily cradle cap, the composition is optimally applied for a period of about 5 minutes, after which the scalp is massaged and the patient's scabs or flakes are removed along with the composition.

1 Claim, No Drawings

SKIN TREATMENT COMPOSITIONS AND METHODS OF USE

SPECIFICATION

CROSS-REFERENCE TO RELATED APPLICATIONS

Not Applicable

STATEMENT REGARDING FEDERALLY SPONSORED RESEARCH OR DEVELOPMENT

Not Applicable

PARTIES TO A JOINT RESEARCH AGREEMENT

Not Applicable

REFERENCE TO SEQUENCE LISTING, A TABLE, OR A COMPUTER PROGRAM

LISTING COMPACT DISK APPENDIX
Not Applicable

BACKGROUND OF THE INVENTION

The invention relates generally to the field of skin treatment compositions and their methods of use, and specifically to compositions and methods of use for treating atopic eczema and cradle cap (infantile or neonatal seborrhoeic dermatitis) in infants and babies. Castor oil has long been used in traditional cultures around the world as a treatment for skin conditions generally; however, in such societies castor oil is not generally applied to infants and babies. The prior art also discloses numerous skin treatment compositions in which any of a number of plant-derived oils, including castor oil may be added to an active ingredient to improve the performance of the composition.

In addition, castor oil has been shown to have antifungal, antimicrobial, anti-inflammatory, and pain reducing properties. In particular, ricineloic acid, a fatty acid only known to occur naturally in castor oil, is thought to be responsible for castor oil's antifungal properties. At the same time, current research suggests that at least some forms of seborrhoeic dermatitis that resist conventional treatment have a fungal cause. The current state of medical practice would suggest avoiding the application of fatty oils to fungal infections because the fungi may extract nutrients from the fat and worsen the infection; however this effect is not known to occur with castor oil in particular.

Absent from the prior art, however, are compositions and methods employing castor oil itself as an active ingredient in treating atopic eczema and cradle cap in infants and babies.

Additionally, the prior discloses numerous references where any of a number of vegetable-derived oils, including castor oil, may be added to mineral oil to create an improved mechanical lubricant. Such compositions, however, are primarily constituted of mineral oil and feature a vegetable-derived oil or other ingredient only as an additive in small amounts.

The following disclosure discusses a heretofore unknown use of castor oil, and in particular novel compositions of castor oil and mineral oil, in treating atopic eczema and cradle cap in infants and babies. Since these skin conditions are extremely common in developed countries and growing more common year by year, there is great commercial potential in treatment methods and compositions produced from components that are inexpensive, readily available, and known to be safe for external use in humans, including infant humans.

SUMMARY OF THE INVENTION

Accordingly, the invention is a new use of castor oil in treating atopic eczema and cradle cap in infants and babies. In the disclosure, castor oil itself is identified as an effective active ingredient. Compositions of greater than fifty percent castor oil and less than fifty percent mineral oil demonstrate a reduced viscosity as compared with pure castor oil, giving these compositions a preferable consistency for skin application. Compositions of approximately 80% castor oil and 20% mineral oil are presently considered optimally viscous for application. The compositions are best applied using a relatively small pump-spray bottle (optimally about 2 oz.) having a relatively small output aperture (optimally about 3 mm). The spray application and improved composition reduce the messiness of the application process.

The composition is applied differently to different conditions; specifically the composition is applied to atopic eczema and dry or non-oily cradle cap and left in place to be absorbed into the patient's skin; to oily cradle cap, the composition is optimally applied for a period of about 5 minutes, after which the scalp is gently massaged and the patient's scabs or flakes removed along with the composition. The application may then be repeated to remove any remaining scabs, and a final application may be left on the patient's scalp and allowed to absorb.

It is an object of the invention to provide a treatment for atopic eczema and cradle cap using inexpensive and readily available components.

It is an object of the invention to provide a treatment for atopic eczema and cradle cap using only components known to be safe for external use in human infants and babies.

It is an object of the invention to provide a treatment method for atopic eczema and cradle cap that may be easily understood and performed at home by an infant's parents or caretakers.

It is an object of the invention to provide a treatment kit for eczema and cradle cap comprising the aforementioned composition, a small pump-spray bottle, and optional absorbent applicators.

It is an object of the invention to provide a treatment kit and method for eczema and cradle cap that allows parents and caretakers to apply and perform a treatment procedure without generating a mess of skin product in the area where the treatment is performed.

Additional features and advantages of the invention will be set forth in the description which follows, and will be apparent from the description, or may be learned by practice of the invention. The foregoing general description and the following detailed description are exemplary and explanatory and are intended to provide further explanation of the invention.

BRIEF DESCRIPTION OF THE DRAWINGS

No drawing is provided for the disclosed invention because a drawing is not necessary for the understanding of the invention under 35 U.S.C. § 113, 37 C.F.R. § 1.81(a), and MPEP § 608.02 (III) (A), (B).

DETAILED DESCRIPTION OF THE INVENTION

Referring now to the invention in more detail, the invention concerns the use of castor oil to treat atopic eczema and cradle cap (infantile or neonatal seborrhoeic dermatitis). For the purposes of the disclosure, "eczema" refers to common atopic eczema occurring in infants and babies, presenting typically with dry and reddened areas of skin on regions other than the scalp. "Dry or non-oily cradle cap" refers to symptoms similar to eczema in infants and babies occurring on the scalp. "Oily cradle cap" refers to oily dry skin and yellow scabs occurring in infants and babies on the scalp. The inventor has observed that castor oil, applied externally to the affected skin area, is an effective active ingredient in the treatment of the aforementioned skin conditions, with each condition being resolved more rapidly as compared with leaving the condition to resolve itself.

Castor oil by itself is too thick and viscous for easy application to a patient's skin. The addition of mineral oil reduces the viscosity of the composition making it easier to spread on the patient's skin. Compositions having at least 50% castor oil and at most 50% mineral oil were observed to provide a treatment benefit. A composition having approximately 80% castor oil and 20% mineral oil was observed to have an optimal consistency for application to skin. Such additional ingredients as may be well known in the art of skin application or other ingredients may, of course, be added with no known deleterious effect on the treatment value of the composition.

The composition is best applied in small manageable quantities; this facilitates targeted application and avoids a mess involving the composition and its residue getting on articles and furniture in the area where the treatment is performed. The composition was placed in a palm-sized (approximately 2 oz.) pump-spray bottle, of the kind well known in the art for packaging such compositions as hair spray, perfume, insect repellant, and the like. The particular pump spray bottle used employed an output aperture of 3 mm, and the aperture may be increased or decreased to change the size of the stream or droplets emerging from the bottle, according to user preference.

Actuating the pump-spray function directed at and in proximity to the affected skin area of a patient resulted in an oily film on the skin made up of the present composition. The small size of the spray bottle made it easily manipulable for precise application to the desired area. The resulting film was runny enough that it could easily be spread by hand, cloth, cotton swab or similar article over the affected area, however it was viscous enough so as not to run unacceptably away from the target area to cause a mess.

For optimal application, the invention may be distributed as a kit including a quantity of the composition and the above-described pump-spray bottle. The composition may be pre-packaged in the pump-spray bottle itself, or may be packaged in a larger container from which the pump spray bottle may be filled. The kit may also include wipe cloths, cotton swabs, or other absorbent articles for use in applying and spreading the composition over the skin.

For treating eczema and dry or non-oily cradle cap, the invention is applied to the affected area of the patient's skin (in the case of dry or non-oily cradle cap, the scalp) directly or using the provided pump-spray bottle and/or applicators. The composition is left on the skin to be absorbed. Improvement or dissipation of the symptoms is then expected shortly thereafter. The process may be repeated as often as desired, such as whenever the skin condition remains in the affected area and the composition is no longer visibly present on the surface of the skin. Since the components, castor oil and mineral oil, are known to be safe for external use, there is no known limit to the frequency of application.

For treating oily cradle cap, the invention is applied to the patient's scalp directly or using the provided pump-spray bottle and/or applicators. The composition is left on the skin for a waiting period. The waiting period, at a minimum, should last several minutes. Five minute waiting periods were found to be sufficient and optimal, however there is no known upper limit to the waiting period. After the expiration of the waiting period, the patient's scalp is gently massaged. For infants 3 months old and younger, the caretaker should massage the scalp with one or more fingers in a circular motion. For infants and babies who are older than 3 months, the caretaker may perform the massage with one or more fingers or with a gentle baby brush. The massaging process removes the yellow scabs that are symptomatic of oily cradle cap without harming or causing pain to the patient. The removed scabs collect on the fingers or brush, which may then be cleaned to avoid creating a mess. The applied composition will have mostly been absorbed into the then-removed scabs leaving relatively little on the patient's scalp. The process may be repeated to remove any remaining scabs. After all of the scabs are removed, the composition may be applied once more and left on as in treating eczema or dry or non-oily cradle cap.

Using the above-described compositions and methods, the increasingly common skin conditions of eczema and cradle cap may be effectively treated. The compositions and kit are simple, inexpensive, readily available, and safe for external use. The methods are simple and easy for a parent or caretaker without special medical training to understand and perform, and to perform without creating a mess.

While the foregoing written description of the invention enables one of ordinary skill to make and use what is presently considered to be the best mode thereof, those of ordinary skill in the art will understand and appreciate the existence of variations, combinations, and equivalents of the specific embodiment, method, and examples herein. The invention should, therefore, not be limited by the above described embodiment, method, and examples, but by all embodiments and methods within the scope and spirit of the invention.

I claim:

1. A method for treating eczema, non-oily cradle cap or oily cradle cap in a patient in need thereof consisting essentially of administering to said patient in need thereof therapeutically effective amounts of castor oil and mineral oil.

* * * * *